US009493147B1

(12) United States Patent
Shoffner et al.

(10) Patent No.: US 9,493,147 B1
(45) Date of Patent: Nov. 15, 2016

(54) AUTOMATED SMEAR MAKING APPARATUS

(71) Applicant: Abbott Laboratories, Abbott Park, IL (US)

(72) Inventors: John Scott Shoffner, San Jose, CA (US); Koshy T. Chacko, San Jose, CA (US); Roei Solomon, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 15/150,111

(22) Filed: May 9, 2016

Related U.S. Application Data

(63) Continuation of application No. 14/692,507, filed on Apr. 21, 2015, now Pat. No. 9,335,334, which is a continuation of application No. 13/725,763, filed on Dec. 21, 2012, now Pat. No. 9,011,773.

(60) Provisional application No. 61/581,032, filed on Dec. 28, 2011.

(51) Int. Cl.
*G01N 21/00* (2006.01)
*B60T 15/00* (2006.01)

(52) U.S. Cl.
CPC ..................................... *B60T 15/00* (2013.01)

(58) Field of Classification Search
CPC .................. G01N 1/2813; G01N 2035/00039
See application file for complete search history.

(56) References Cited

U.S. PATENT DOCUMENTS

| | | | |
|---|---|---|---|
| 3,991,705 | A | 11/1976 | Adler |
| 4,027,623 | A | 6/1977 | Adler |
| 4,137,866 | A | 2/1979 | Heanley et al. |
| 4,269,139 | A | 5/1981 | Adler et al. |
| 5,854,075 | A | 12/1998 | Levine et al. |
| 6,319,470 | B1 | 11/2001 | Lefevre et al. |
| 2003/0138355 | A1 | 7/2003 | Tamura et al. |
| 2007/0140903 | A1 | 6/2007 | Jin et al. |
| 2008/0193926 | A1 | 8/2008 | Abraham-Fuchs et al. |

*Primary Examiner* — Jyoti Nagpaul
(74) *Attorney, Agent, or Firm* — Edward J. Baba; Brian E. Davy; Bozicevic, Field & Francis LLP

(57) ABSTRACT

An automated smear making apparatus used to prepare and smear samples on glass slides. In one embodiment, there is provided a smearing subsystem that generally includes a smear cartridge having: an input reel; at least one roll bar; a take-up reel; and a smearing tape. The smearing tape is initially wound within the input reel and coupled to the take-up reel such that the smearing tape can be drawn from the input reel and into the take-up reel. The smearing tape may include a plurality of perforations formed therein. The smearing tape may then be wrapped around the roll bar such that each of the plurality of perforations forms a blade that extends from the smearing tape to expose a smear surface as the smearing tape is drawn into the take-up reel. Alternatively, the smearing tape may be bent such that an edge of the smearing tape forms a smear surface between two roll bars. A slide transport surface is also provided to move a slide across the smear surface.

20 Claims, 8 Drawing Sheets

AUTOMATED SMEAR MAKING APPARATUS

CROSS REFERENCE TO RELATED APPLICATIONS

This application is a continuation of U.S. patent application Ser. No. 14/692,507, filed on Apr. 21, 2015, now U.S. Pat. No. 9,335,334, which is a continuation of U.S. patent application Ser. No. 13/725,763, filed on Dec. 21, 2012, now U.S. Pat. No. 9,011,773, which claims priority to U.S. Provisional Patent Application No. 61/581,032, filed on Dec. 28, 2011, the disclosures of which are herein incorporated by reference in their entirety.

BACKGROUND

The present disclosure generally provides an automated smear making apparatus used to prepare and smear samples (e.g., blood samples) on microscope slides. In one embodiment, there is provided a smearing subsystem for use in an automated slide preparation apparatus. The smearing subsystem generally includes a smear cartridge having an input reel, a deflection component, a take-up reel, and a smearing tape to form a smear surface. The smearing tape is initially wound within the input reel and coupled to the take-up reel such that the smearing tape can be drawn from the input reel and into the take-up reel. The smearing tape may include a plurality of perforations formed therein. The smearing tape may then be deflected by the deflection component such that each of the plurality of perforations forms a blade that extends from the smearing tape to expose a smear surface as the smearing tape is drawn into the take-up reel. In an alternative embodiment, an edge of the smearing tape may be used to form the smear. For example, the smearing tape may be manipulated such that an edge of the smearing tape forms a smear surface between a first and a second deflection component. The angle between the smearing tape edge and the slide may be adjusted either by a mechanical mechanism or by the first and/or second deflection components. A slide transport surface is also provided to move a microscope slide across the smear surface.

Additional embodiments and details are provided below.

SUMMARY

In some embodiments, the present disclosure provides a smearing subsystem for use in an automated slide preparation apparatus, the smearing subsystem including a smear cartridge including an input reel, a take-up reel, a smearing tape having a plurality of perforations formed therein, wherein the smearing tape is initially wound within the input reel and coupled to the take-up reel such that the smearing tape can be drawn from the input reel into the take-up reel, a deflection component configured to deflect each of the plurality of smearing tape perforations to create a blade that extends from the smearing tape to expose a smear surface as the smearing tape is drawn into the take-up reel, and a slide transport surface configured to move a slide across the exposed smear surface.

In some embodiments, the blade forms an acute angle with the slide when the slide transport surface brings the slide in contact with the exposed smear surface. In some embodiments, the smearing subsystem further includes an angle-control mechanism to adjust the acute angle formed between the blade and the slide. In some embodiments, the angle-control mechanism is configured to adjust the position of the deflection component with respect to the input reel. In some embodiments, the angle-control mechanism is configured to adjust the position of the deflection component with respect to the take-up reel. In some embodiments, the angle-control mechanism includes a step motor configured to move the deflection component. In some embodiments, the angle-control mechanism is configured to adjust the position of the input reel with respect to the deflection component. In some embodiments, the angle-control mechanism is configured to adjust the position of the take-up reel with respect to the deflection component. In some embodiments, the acute angle is less than about 60 degrees. In some embodiments, the acute angle is less than about 45 degrees. In some embodiments, the acute angle is less than about 30 degrees. In some embodiments, the acute angle is less than about 15 degrees.

In some embodiments, the present disclosure provides a smearing subsystem for use in an automated slide preparation apparatus, the smearing subsystem including a smear cartridge including an input reel, a first and a second deflection component, a take-up reel, a smearing tape, wherein the smearing tape is initially wound within the input reel and coupled to the take-up reel such that the smearing tape can be drawn from the input reel into the take-up reel, and wherein the smearing tape is disposed around the first and second deflection components, between the input reel and the take-up reel such that an edge of the smearing tape forms a smear surface between the first and the second deflection components, and a slide transport surface configured to move a slide across the smear surface. In some embodiments, the first and the second deflection components bend the smearing tape such that an acute angle is formed between the smearing tape and the slide when the slide transport surface brings the slide in contact with the smear surface. In some embodiments, the smearing subsystem further includes an angle-control mechanism to adjust the bend of the smearing tape between the first and the second deflection components. In some embodiments, the angle-control mechanism is configured to adjust the position of one of the first or the second deflection component. In some embodiments, the angle-control mechanism is configured to adjust the position of both the first and the second deflection components. In some embodiments, the first and the second deflection components are parallel to one another. In some embodiments, the movement of the slide transport surface is perpendicular to the smearing tape. In some embodiments, the acute angle is less than about 60 degrees. In some embodiments, the acute angle is less than about 45 degrees. In some embodiments, the acute angle is less than about 30 degrees. In some embodiments, the acute angle is less than about 15 degrees. In some embodiments, the first deflection component comprises a roll bar, and the smearing tape is wrapped around the roll bar between the input reel and the take-up reel. In some embodiments, the second deflection component comprises a roll bar, and the smearing tape is wrapped around the roll bar between the input reel and the take-up reel.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the systems and methods presented. In the drawings, like reference numbers indicate identical or functionally similar elements.

DETAILED DESCRIPTION

The present invention relates to automated slide preparation systems used to prepare, smear, and image samples (e.g., blood samples) on microscope slides. In one particular embodiment, there is provided a low-cost smearing subsystem for use in an automated slide preparation system. Such smearing subsystem employs a reel-to-reel configuration to provide a single use smear surface from a smearing tape (or ribbon). More specifically, a smearing tape, which is initially wound within an input reel, is configured to provide multiple smearing edges (or surfaces) for the smearing of a series of slides, as it is unwound from the input reel and drawn into a take-up (or waste) reel. The reel-to-reel configuration is indexed to move (or advance) the tape such that a subsequent, clean smear surface is provided for a subsequent slide. As such, the smearing subsystem prevents cross-contamination, and possible operator biohazard, by continuously providing clean, single-use smear surfaces. Various embodiments are described below.

For example, in one embodiment, the smearing subsystem generally includes a smear cartridge having an input reel, a deflection component, a take-up reel, and an indexed smearing tape. The smearing tape is initially wound within the input reel. The smearing tape is coupled to (or at least partially wound within) the take-up reel such that the smearing tape can be drawn from the input reel into the take-up reel. In one embodiment, the smearing tape may include a plurality of perforations formed therein. The smearing tape is then wrapped around (or otherwise disposed on or stretched around) the deflection component such that each of the plurality of perforations creates a blade that extends from the smearing tape to expose a smear surface as the smearing tape is drawn into the take-up reel. In an alternative embodiment, an edge of the smearing tape may be used to form the smear. For example, the smearing tape may be manipulated such that an edge of the smearing tape forms a smear surface between a first and a second deflection component. The angle between the tape edge and the slide may be adjusted either by a mechanical mechanism or by the first and the second deflection components. In some embodiments, the first and/or the second deflection components may comprise a roll bar, and the smearing tape may be wrapped around (or otherwise disposed on, mounted on, or wound or stretched around) the roll bar. A slide transport surface is also provided to move a microscope slide across the smear surface.

The following detailed description of the figures refers to the accompanying drawings that illustrate one or more exemplary embodiments. Other embodiments are possible. Modifications may be made to the embodiment described herein without departing from the spirit and scope of the present invention. Therefore, the following detailed description is not meant to be limiting.

Figure 1:
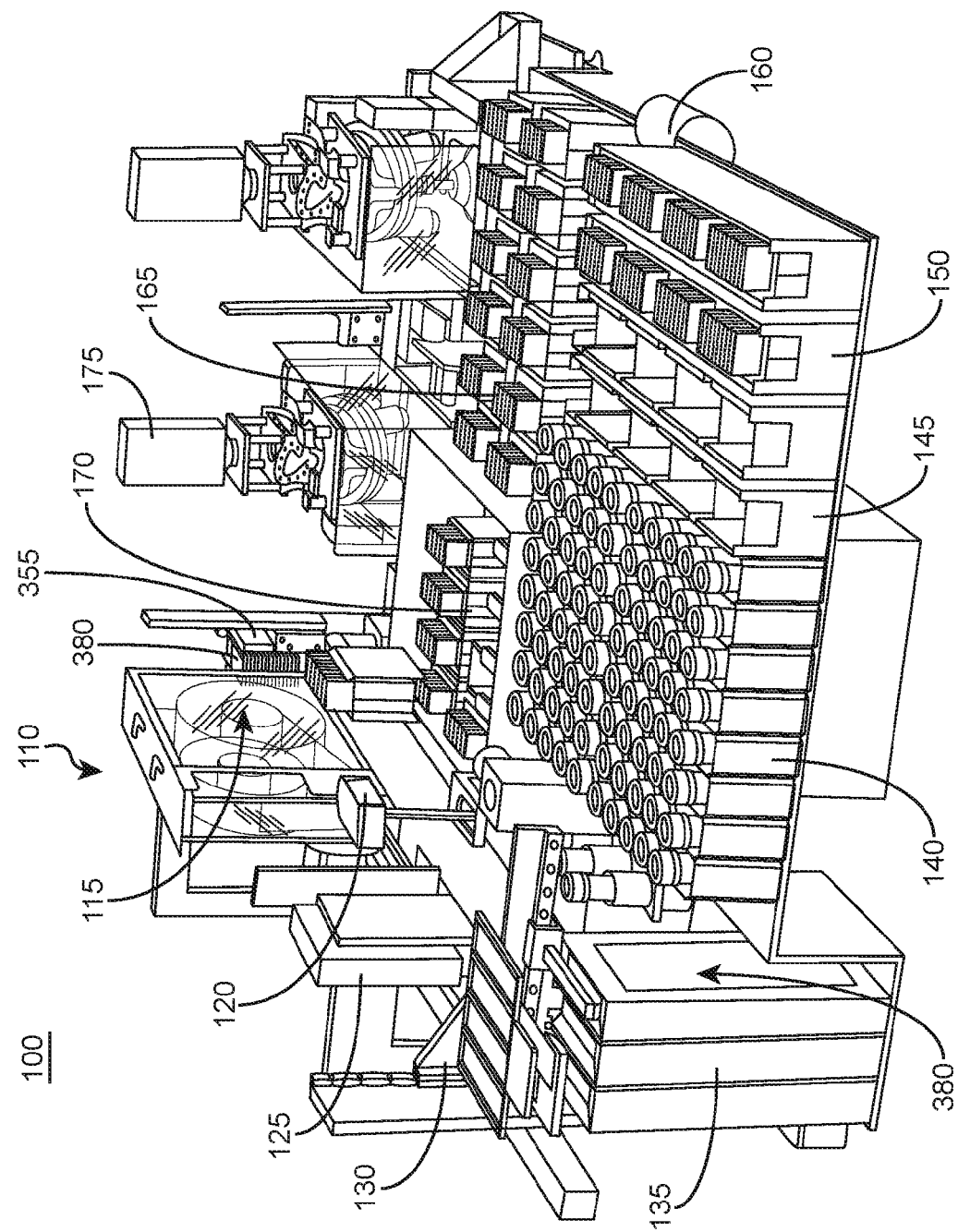
FIG. 1 is a perspective view of an automated slide preparation apparatus.

FIG. 1 is a perspective view of an automated slide preparation apparatus 100, which is used to deposit a sample (e.g., a blood sample) onto a slide 380 (e.g., a glass, plastic, quartz, or other microscope slide), smear the sample for optimal viewing, and/or stain and dry the sample prior to imaging the slide. In the embodiment shown, the slide preparation apparatus 100 includes a smearing cartridge 115, a sample aspiration subsystem 120, a slide printer and barcode subsystem 125, and a slide transfer subsystem 130. In operation, the slide transfer subsystem 130 draws slides 380 from one or more slide holders 135, and transports the slides 380 to the sample aspiration subsystem 120. At the sample aspiration subsystem 120, a drop of sample (e.g., blood) is applied to the slide 380 via an aspiration probe 221. The aspiration subsystem 120 may draw samples (and if necessary reagents) from one or more tube rack inputs 140.

After the slide 380 has been processed through the smearing cartridge 115, where the sample is smeared across the slide 380, the smeared slide is transported to a slide carrier (or cartridge) 355, which has one or more empty locations to accommodate a slide 380. (A plurality of slide carriers 355, having one or more empty locations to accommodate slides 380, are maintained in holding area 145.) Next, the slide carrier 355, typically holding a plurality of smeared slides 380, is further processed through additional subsystems, such as a staining subsystem 170 and/or a drying subsystem 165. In the staining subsystems, the slides 380 are subjected to various reagents and/or cleaning baths. Finally, the slides 380 are processed through an imaging subsystem 175, where the samples are imaged for viewing by a trained professional and/or a computer-automated imaging analysis system.

Figure 2:
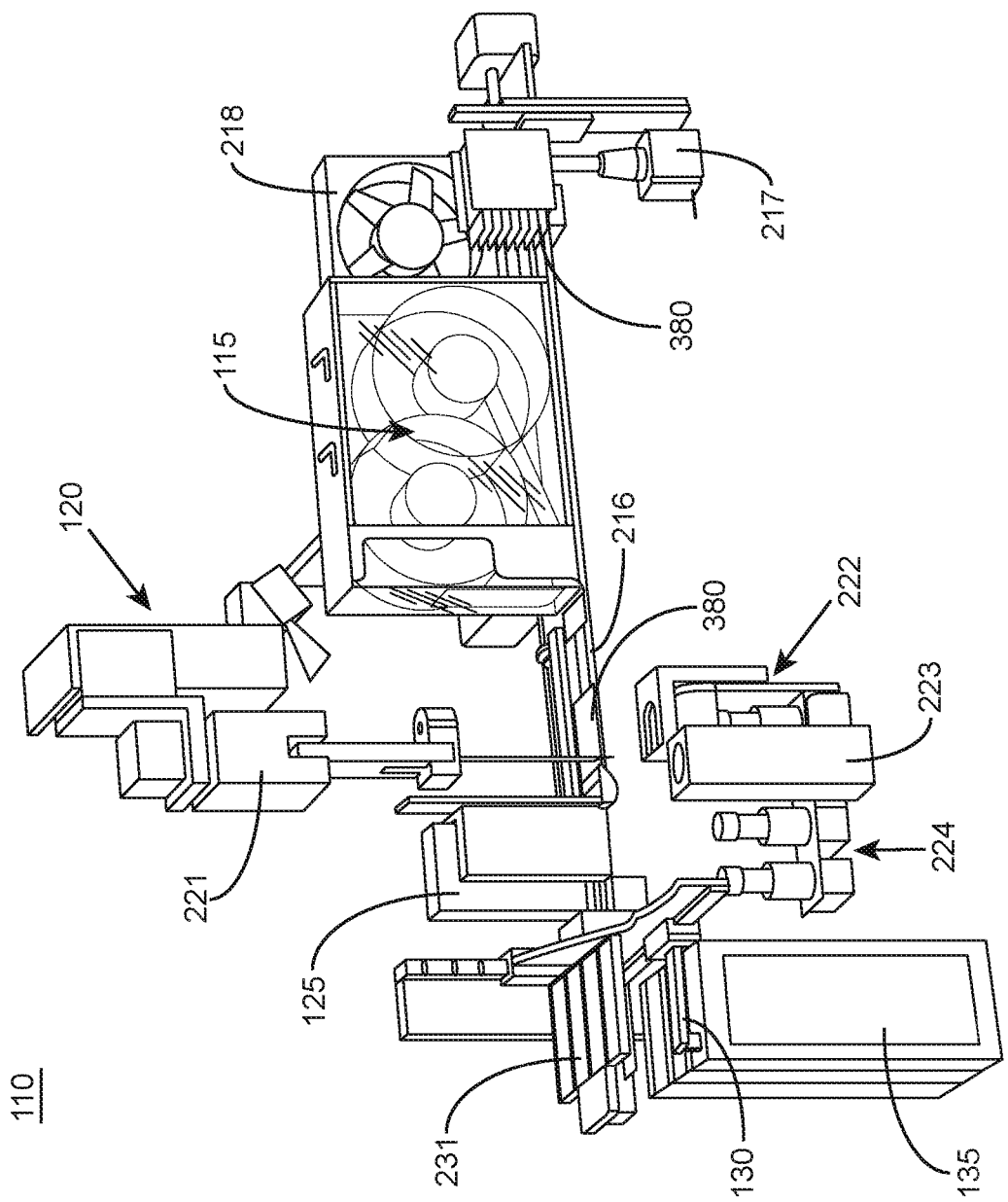
FIG. 2 illustrates a smearing subsystem for use in an automated slide preparation apparatus.

FIG. 2 provides perspective view of the smearing subsystem 110 of FIG. 1. More specifically, FIG. 2 shows additional details of the sample aspiration subsystem 120, which includes an aspiration shuttle (or probe) 221, an aspiration point 222, a wash block 223, and a re-suspension unit 224. In operation, a slide 380 is drawn from the slide holders 135 (or externally prepared slide input mount 231). A label (or other indicia such as a barcode) may be applied to the slide 380 within the printer and barcode subsystem 125. The slide 380 is then moved from the aspiration subsystem 120 to the smear cartridge 115 over a slide transport surface 216. After being smeared, the slide 380 is moved to a slide carrier (or cartridge) 355, which may be indexed by rack in a vertical indexer 217. As the slides 380 are mounted onto the slide carrier 355, a drying fan 218 may be applied to the slides 380.

Figure 3:
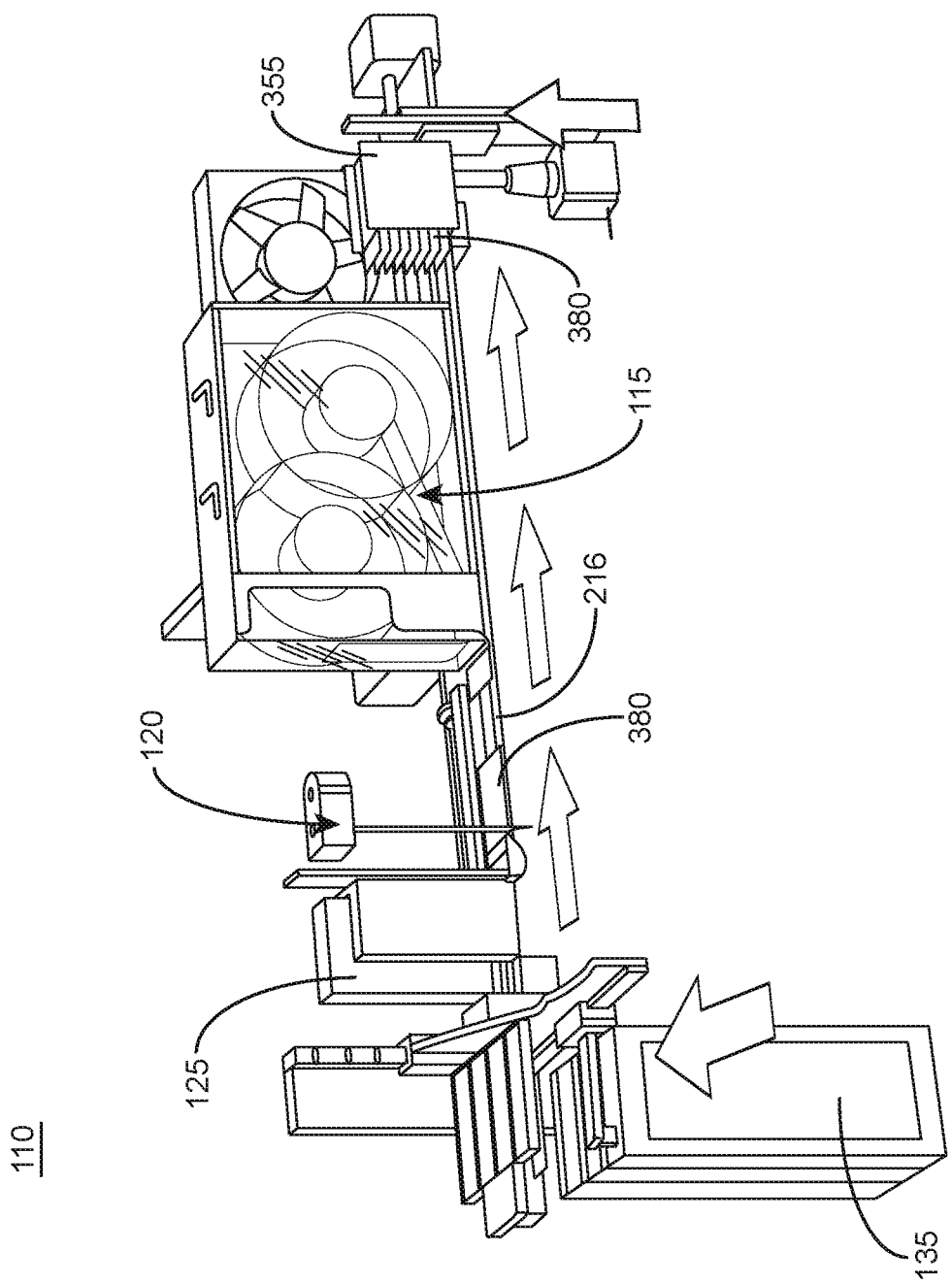
FIG. 3 is a perspective view of the smearing subsystem of FIG. 2.

FIG. 3 provides another perspective view of the smearing subsystem 110 of FIG. 1. More specifically, the arrows of FIG. 3 show the process flow of a slide 380 as it is taken from the slide holders 135, through the sample aspiration subsystem 120, the smearing cartridge 115, and deposited onto the slide carrier 355. Additional details of the slide carrier 355 are disclosed in U.S. Provisional Application No. 61/581,037, the entire disclosure of which is incorporated by reference herein.

Figure 4A:
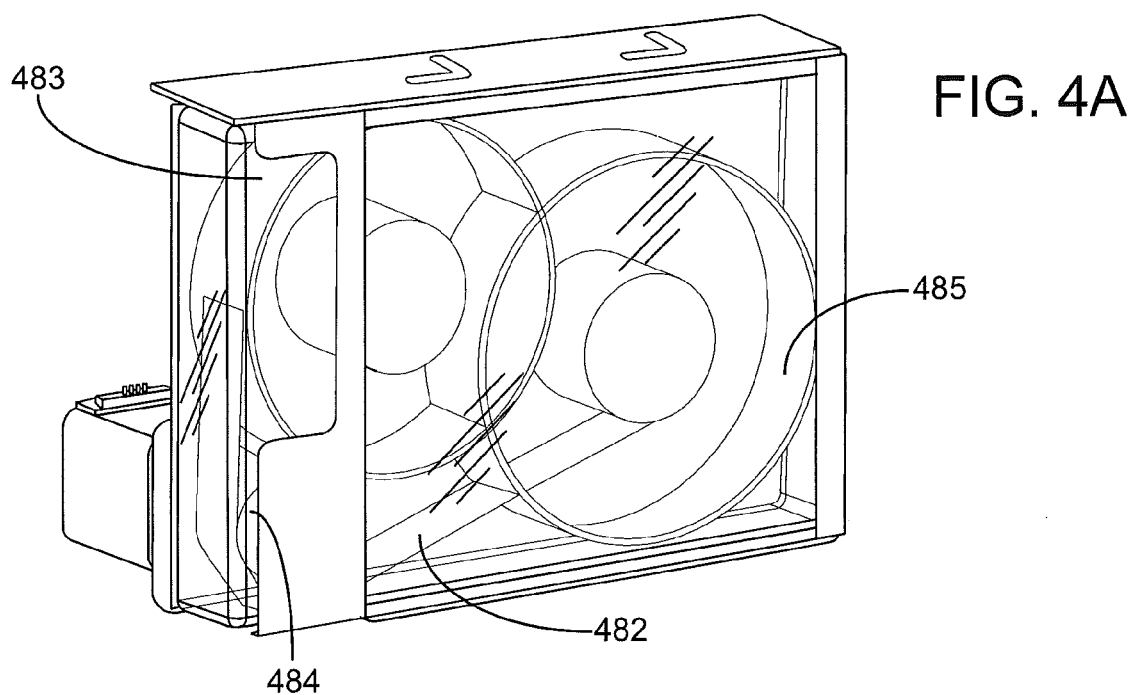
FIGS. 4A and 4B show a perspective view of a smearing cartridge in accordance with one embodiment presented.
Figure 4B:
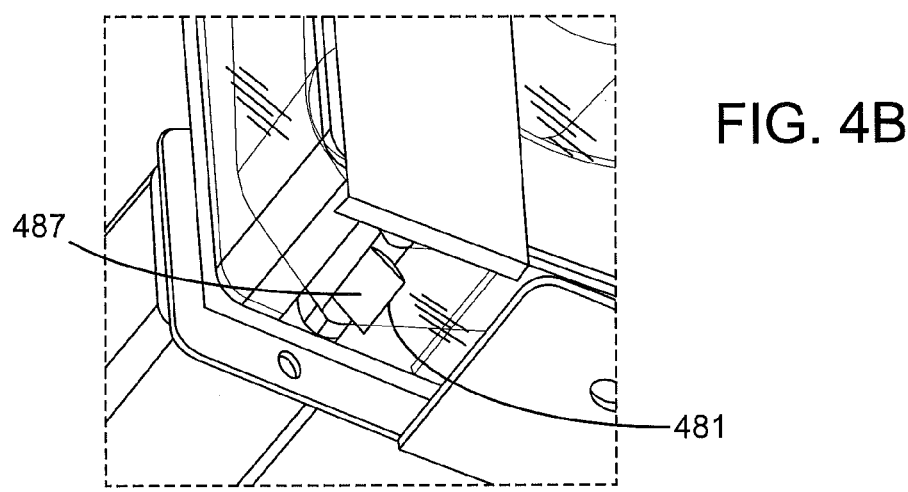

FIG. 4A is a perspective view, and FIG. 4B is a bottom-side view of a smearing cartridge 115, in accordance with one embodiment presented. As shown, a smear surface 481 is provided by a blade (or tab, or projection) 487 extending from a smearing tape 482. The blade 487 extends from the smearing tape 482 as the smearing tape is drawn from the input reel 483, around a deflection component, such as, e.g., a roll bar (or roller) 484, and into the take-up reel 485. In practice, the smearing tape 482 may be indexed to provide controlled movement of the tape. A motor (such as a step motor) may be coupled to the take-up reel 485 to provide the movement of the smearing tape 482. In some embodiments, an adjustment mechanism, such as, e.g., a motor or a brake, may be applied to the input reel 483 to provide appropriate tension on the smearing tape 482. Adjustment mechanisms may also be provided to adjust the relative positioning between the input reel 483, the deflection component(s), and/or the take-up reel 485.

Figure 5A:
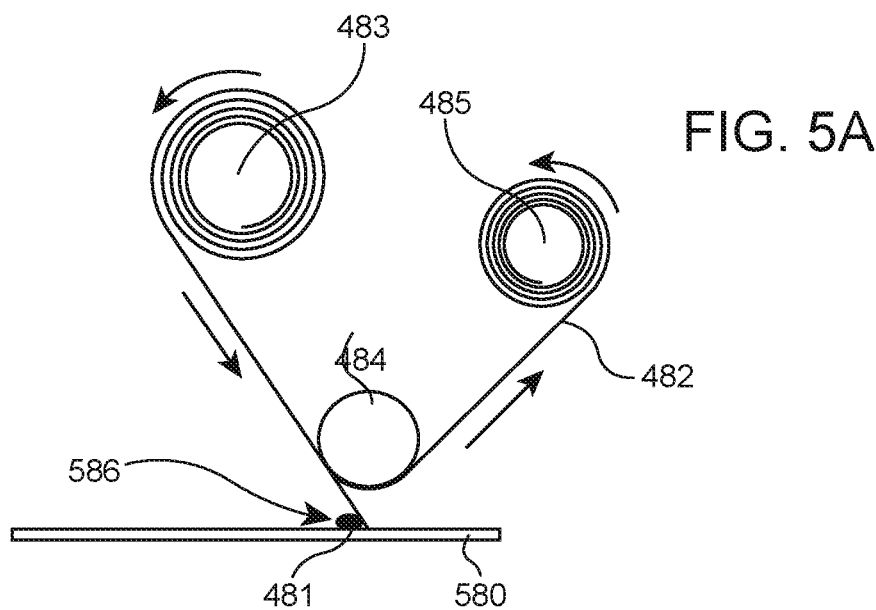
FIGS. 5A and 5B show a schematic illustration of an input reel, deflection component, take-up reel, and smearing tape.
Figure 5B:
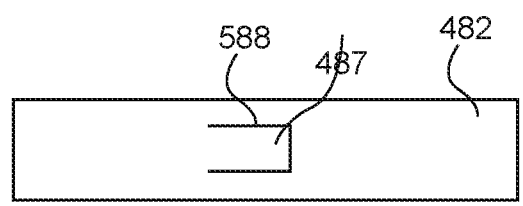
Figure 5B:
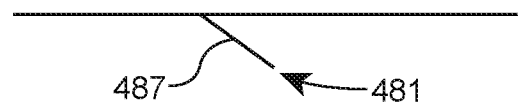

FIGS. 5A and 5B show a schematic illustration of how the blades (or tabs, or projections) 487 extend from the smearing tape 482 as the smearing tape wraps (or is otherwise disposed or stretched) around a deflection component. More specifically, a perforation (or cut-out) 588 is created within the smearing tape 482 such that the change in direction of the smearing tape around the deflection component causes the blade 487 to project (or extend) from the smearing tape 482, and thereby creates a single-use smear surface 481. The smear surface 481 is then used to smear a drop of sample (e.g., blood) 586, which is disposed on a slide 580, as the slide transport surface moves the slide across the smear surface 481. After the slide 580 has been smeared, the smearing tape 482 is advanced by drawing the smearing tape into the take-up reel 485. The blade 487 returns from its extended position as the smearing tape 482 moves beyond the deflection component. The ensuing blade on the smearing tape 482 is then used for the next slide to be processed.

In one embodiment, the smearing tape 482 includes a plurality of indexing holes for "tractor feeding" of the tape, which do not directly influence the function of the blades 487. These indexing holes may be round, but their shape may change to slots to accommodate tolerances, or even notches in the edge of the tape to prevent waste "slugs" of material needing to be removed in processing. The key aspect of the indexing is to provide a means for an accurate tape location determination. In one embodiment, perforations (or cut-outs) to create the blades create a flat section (i.e., inside "critical edge") that dictates the width of the smear. In one embodiment, the width of the smear is 25 mm, with a critical edge 22 mm wide, and an R1.5 in each corner. In one embodiment, the critical edge is smooth and free of burrs. In one embodiment, the perforation itself creates a 2.5 mm cut-out to create the blade profile. Such cut-out may be as small as possible to minimize tape usage, and as large as possible to maximize punch tooling robustness. The cut-out width dimension may also be zero (i.e., a shear cut). Cut-outs in the tape may be created by die-cutting, while several variants are available such as: flatbed kiss cutting against sacrificial anvil using "steel rule" die; rotary kiss cutting against anvil using one-sided rotary die; rotary kiss cutting against anvil and temporary "low tack" backing using one-sided rotary die; flatbed "match metal" or "male-female" die set; and/or rotary "match metal" or "male-female" die set.

Candidate materials for the smearing tape 482 include a number of semi-rigid thermoplastic polymers, including: Acrylonitrile Butadiene Styrene (ABS); polyethylene (PE; also known as: HDPE, MDPE, LDPE, LLDPE); polystyrene (PS); polypropylene (PP); polyurethane (PU); polyamide (PA, commonly known as Nylon); polyoxymethylene (POM, commonly known as Acetal or by trade name Delrin®); polycarbonate (PC); polytetrafluoroethylene (PTFE, commonly known by the trade name Teflon®); polyethylene terephthalate (PET, commonly known as polyester or by the trade names Mylar® or Melinex®); polyvinyl chloride (PVC, commonly known as Vinyl); poly-methyl methacrylate (PMMA, commonly known as Acrylic or by the trade names Perspex® or Plexiglass®).

In some embodiments, the smearing tape may comprise a plastic film that has a hydrophilic coating or a hydrophobic coating. In some embodiments, the smearing tape may comprise a plastic film that has been treated with a mild acid, such as, e.g., citric acid or isopropyl alcohol, to facilitate good wicking and smearing of a sample onto a substrate, such as a glass slide.

In some embodiments, the material for the smearing tape may be polyester (PET) because of its toughness and stability. Polyester film is available with a range of properties mainly in terms of optical clarity and treatment for adhesion to various substrates. The indirect influence of surface finish is important in promoting wicking of the blood drop across the width of the blade.

The length of the individual blades 487 (i.e., the "spine" area at the back of the blade) and the thickness of the smearing tape 482 material may dictate the stiffness of the blade 487 as well as the sensitivity to angular position as the smearing tape wraps around (or bends around, or contacts) the deflection component. The gauge of the smearing tape material may be 175 μm (0.007"), while alternatives are available, such as a range from 75-250 μm.

Figure 6:
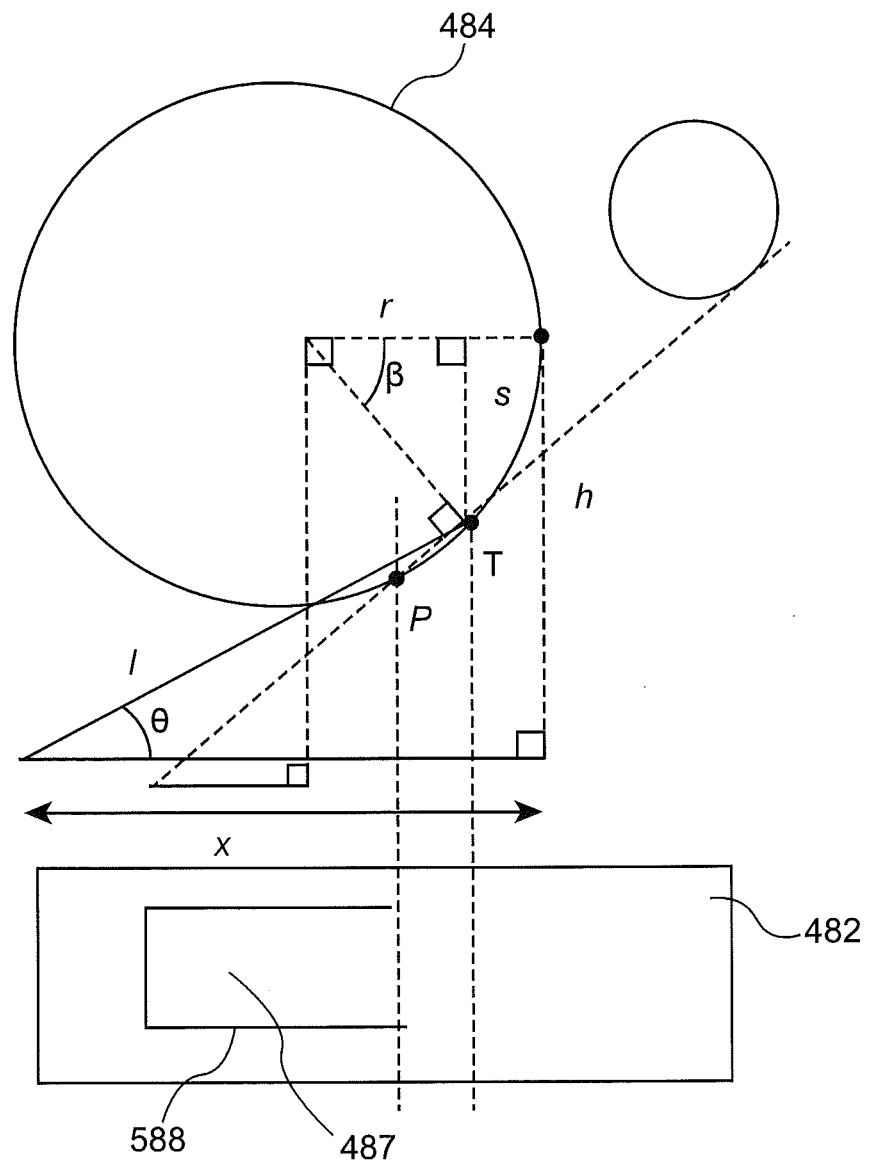
FIG. 6 is a schematic illustration describing one embodiment presented.

FIG. 6 is a schematic illustration describing one embodiment presented. More specifically, FIG. 6 shows the key angles and distances provided for creating optimal smears, which may be affected by factors such as the viscosity of the sample, hematocrit level of the sample, volume of the sample, etc. Smearing may also be sensitive to a number of different parameters that will require tuning of the smearing subsystem to create smears of acceptable quality. Said parameters may be adjusted based on the relative position between the input reel, the deflection component(s), and/or the take-up reel. Parameters that may require adjustment also include: distance between the deflection component(s) and the slide; indexing angle of the smearing tape; velocity profile of the slide; wicking position and time; perpendicularity of the smearing tape relative to the slide; blade pressure against the slide; and/or centering of the blade on the slide.

The simplified geometry shown in FIG. 6 shows parameters defined as follows:

$\theta$=smear blade to slide contact angle
x=distance between front of deflection component and smear blade contact on slide
$\beta$=indexing angle between point P and blade tangent contact
s=arc length between point P and blade tangent contact
h=distance between deflection component center and slide surface (e.g., 8.5 mm)
l=smear blade length (e.g., 10 mm)
r=deflection component radius (e.g., 5 mm)

In one embodiment, it may be assumed that the blade 487 would extend at a perfect tangent from the deflection component (e.g., roll bar 484) when no slide is in place. However, when a slide 580 is inserted, the distance between the deflection component and slide 580 is limited to h, causing the blade 487 to rotate around the tangent point, T. In calculating the geometry, it is assumed that there is no flexing of the blade 487 and it pivots perfectly around the tangent point. In this case, the following geometry is used, when a certain contact angle, $\theta$, is defined.

If $l \sin(\theta) + r \cos(\theta) \geq h$, then:

$$\beta = \sin^{-1}((h - l \sin(\theta))/r)$$

$s=r\beta$ $x=r-r\cos(\theta)+l\cos(\theta)$

In one embodiment, the smearing tape 482 includes one or more optical identifiers or indicia (not shown) to identify the relative position of the smearing tape and or blades. In one embodiment, a distance along the smearing tape between an optical identifier and point P is 16.9 mm, and the distance between indexing holes in the smearing tape is 20.5 mm. As such, the smearing tape index distance, i, is: i=(s+16.9)mod 20.5. In one embodiment, the distance along the slide between the home position and the blood dispense location directly underneath point P is 73 mm. The smear start position, m, where the blade edge contacts the blood is thus: m=x+73

Calculations may be required to determine the number of steps required to index the smearing tape a certain distance given the changing diameter of the input reel and take-up reel, as the smearing tape is advanced. In this case, the size of the reel will follow the equation:

$$R = \sqrt{\frac{Lt}{\pi} + r_2^2}$$

where:
R=radius of reel with tape
L=used length of tape (e.g., number of smears×20.5 mm)
$r_2$=radius of waste reel core (e.g., 12.5 mm)

Figure 7:
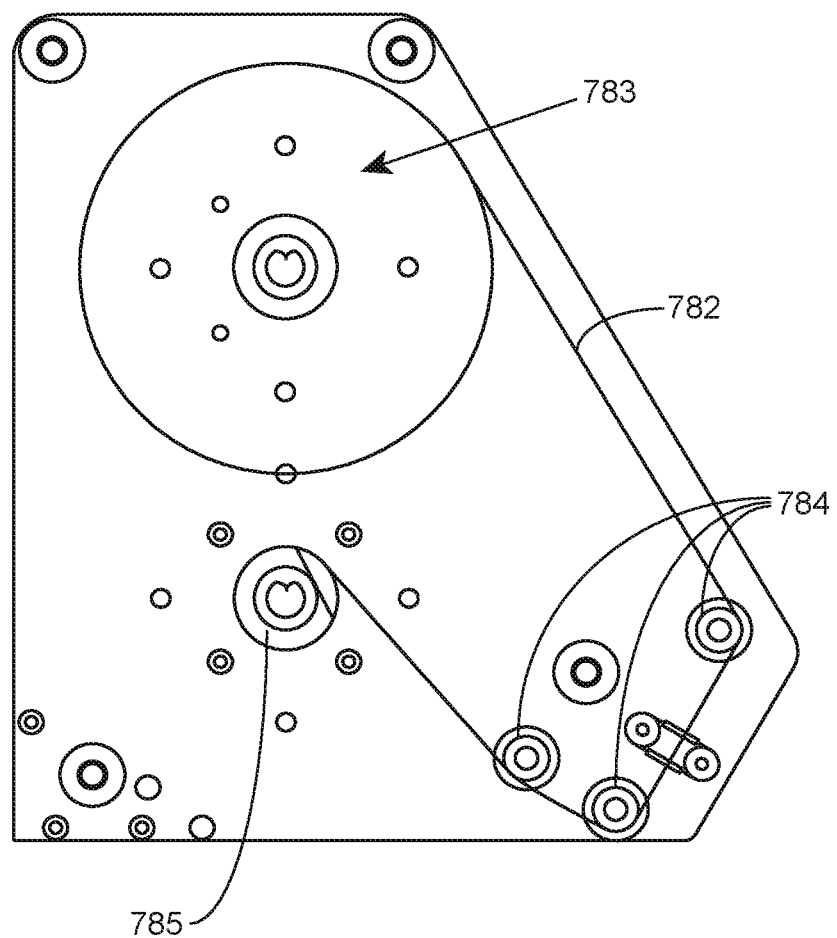
FIG. 7 is a side view of a smearing cartridge in accordance with another embodiment presented.

FIG. 7 is a side view of a smearing cartridge 715, in accordance with another embodiment presented. As shown in FIG. 7, an input reel 783 provides a smearing tape 782 that may be indexed for movement across a plurality of deflection components (e.g., roll bars 784). The smearing tape 782 may be advanced using a stepper motor (not shown) coupled to the take-up (or waste) reel 785. In some embodiments, an adjustable brake or other suitable component, such as, e.g., a motor (not shown) may be attached to the input reel 783 to set the proper tension to the smearing tape 782. The smearing tape 782 may be punched with holes in the side and/or painted with a silver paint pen so that an optical sensor can be used to set the position of the smearing tape when an opening or painted indicia is sensed.

Figure 8:
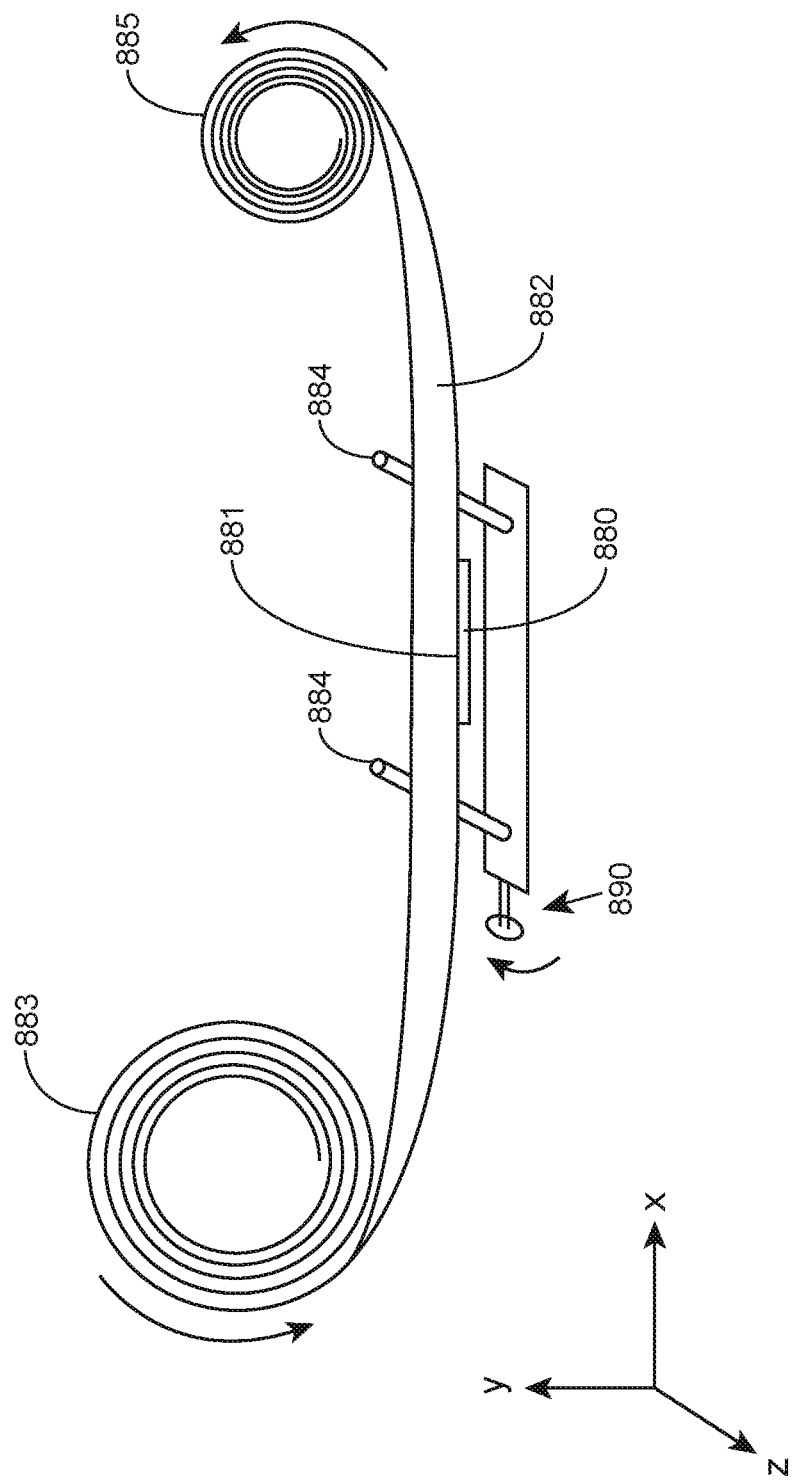
FIG. 8 is a schematic illustration of another embodiment presented.

FIG. 8 is a schematic illustration of another embodiment presented. As shown in FIG. 8, an input reel 883 provides an un-perforated smearing tape 882, which is wrapped around (or bent around, or stretched around or upon, or otherwise disposed about) a first and a second deflection component (e.g., two roll bars 884). The first and the second deflection components function to manipulate (e.g., bend, move, stretch, and or deform) the smearing tape 882 such that an edge of the smearing tape forms a smear surface 881 for smearing a sample on a slide 880. An angle control mechanism 890 may be provided to adjust the angle of the smear surface 881 appropriately. The angle between the smearing tape edge and the slide 880 may be adjusted either by a mechanical mechanism and/or the first and the second deflection components. In operation, a slide transport surface moves the slide 880 perpendicularly (e.g., along the z-axis) across the smear surface 881.

Additional Embodiments

In another embodiment, there is provided a method of smearing a sample in an automated slide preparation apparatus. The method includes providing a smearing subsystem having: a smear cartridge including an input reel, a deflection component (e.g., a roll bar), a take-up reel, and a smearing tape. In one embodiment, the smearing tape may include a plurality of perforations formed therein. The smearing subsystem may be configured such that the smearing tape is initially wound within the input reel and coupled to the take-up reel so that the smearing tape can be drawn from the input reel into the take-up reel. The smearing tape may also be configured to wrap around the deflection component, between the input reel and the take-up reel, such that each of the plurality of perforations creates a blade that extends from the smearing tape to expose a smear surface as the smearing tape is drawn into the take-up reel. The smear surface may then form an acute angle with the slide when the slide transport surface brings the slide in contact with the exposed smear surface. In another embodiment, the smearing tape is bent between a first and a second deflection component such that a side surface of the smearing tape creates the smear surface. The method may further include providing a slide transport surface configured to move a slide across the exposed smear surface (be it the blade or the side of the bent smearing tape). The method may further include configuring the smear cartridge such that the acute angle is less than about 60 degrees, less than about 45 degrees, less than about 30 degrees, and/or less than about 15 degrees. Such configuration may include moving the input reel, the first and/or the second deflection components, and/or the take-up reel with respect to one another. Such configuration may also include monitoring the sample with an optical input subsystem (or other input parameter) to adjust the acute angle depending on properties (e.g., hematocrit level, viscosity, or volume) of the sample. The method may further include adjusting: the distance between the first and/or the second deflection component and the slide; indexing angle of the smearing tape; velocity profile of the slide; wicking position and time; perpendicularity of the smearing tape relative to the slide; and/or centering of the blade on the slide.

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. A method for preparing a slide comprising a sample smear using an automated slide preparation apparatus, the method comprising:
   depositing a sample onto a slide;
   moving the slide towards a smear surface of a smearing tape of a smear cartridge, wherein the smear surface is included on a blade of a cut-out of the smearing tape, and wherein the smearing tape is initially wound within an input reel of the cartridge and coupled to a take-up reel of the smear cartridge;

moving the slide across the smear surface to produce a sample smear, wherein the smear surface is exposed when the position of the blade of the cut-out is extended by a deflection component of the smear cartridge as the smearing tape is drawn from the input reel and into the take-up reel; and drying the sample smear.

2. The method according to claim 1, wherein the sample is deposited onto the slide at an aspiration subsystem of the automated slide preparation apparatus, and prior to depositing the sample onto the slide, the slide is transported from a slide holder to the aspiration subsystem.

3. The method according to claim 2, comprising applying a label to the slide prior to depositing the sample onto the slide.

4. The method according to claim 3, wherein applying a label to the slide comprises printing a label on the slide.

5. The method according to claim 4, wherein the label comprises a barcode.

6. The method according to claim 1, wherein drying the sample smear comprises transporting the slide to a slide carrier and allowing the sample smear to dry in the slide carrier.

7. The method according to claim 1, comprising staining the sample smear subsequent to drying the sample smear.

8. The method according to claim 7, comprising imaging the stained sample smear.

9. The method according to claim 8, comprising analyzing an image of the stained sample smear using an image analysis system.

10. The method according to claim 1, wherein the sample is a blood sample.

11. The method according to claim 1, wherein the deflection component comprises a roll bar.

12. The method according to claim 1, wherein the blade forms an acute angle with the slide when the slide is brought in contact with the exposed smear surface.

13. The method according to claim 12, further comprising adjusting the acute angle formed between the blade and the slide via an angle-control mechanism.

14. The method according to claim 13, wherein adjusting the acute angle comprises adjusting the position of the deflection component with respect to the input reel.

15. The method according to claim 13, wherein adjusting the acute angle comprises adjusting the position of the deflection component with respect to the take-up reel.

16. The method according to claim 13, wherein the angle control mechanism comprises a step motor configured to adjust the deflection component.

17. The method according to claim 13, wherein adjusting the acute angle comprises adjusting the position of the input reel with respect to the deflection component.

18. The method according to claim 13, wherein adjusting the acute angle comprises adjusting the position of the take-up reel with respect to the deflection component.

19. The method according to claim 12, wherein the acute angle is 45 degrees or less.

20. The method according to claim 12, wherein the acute angle is 30 degrees or less.

* * * * *